(12) United States Patent
Redko et al.

(10) Patent No.: US 8,102,181 B2
(45) Date of Patent: Jan. 24, 2012

(54) METHOD AND DEVICE FOR RAPID NON-DESTRUCTIVE QUALITY CONTROL OF POWDERED MATERIALS

(75) Inventors: Volodymyr I Redko, Coral Springs, FL (US); Elena M Shembel, Coral Springs, FL (US); Volodymyr S Khandetskyy, Dnipropetrovsk (UA); Dmytro I Sivtsov, Dnipropetrovsk (UA); Tymofiy V Pastushkin, Ft. Lauderdale, FL (US); Oxana Redko, Dnipropetrovsk (UA); Bary Wilson, Coconut Creek, FL (US)

(73) Assignee: Enerize Corporation, Coral Springs, FL (US)

( * ) Notice: Subject to any disclaimer, the term of this patent is extended or adjusted under 35 U.S.C. 154(b) by 388 days.

(21) Appl. No.: 12/386,588

(22) Filed: Apr. 21, 2009

(65) Prior Publication Data
US 2009/0267621 A1    Oct. 29, 2009

Related U.S. Application Data

(60) Provisional application No. 61/124,984, filed on Apr. 21, 2008.

(51) Int. Cl.
*G01R 27/26* (2006.01)
*G01R 31/02* (2006.01)

(52) U.S. Cl. .................................. 324/682; 324/76.11
(58) Field of Classification Search .................. 324/600, 324/658, 682
See application file for complete search history.

(56) References Cited

U.S. PATENT DOCUMENTS
4,208,624 A * 6/1980 Miller ........................... 324/682
* cited by examiner

*Primary Examiner* — Vincent Q Nguyen

(57) ABSTRACT

Method and related device intended for rapid non-destructive testing of powdered materials with low electric conductivity such as cement and cement-based compositions through determination of their electrical properties. The invention involves an electromagnetic method, including an electronic circuit for generating an electric field in a capacitance probe that is inserted into the powder to be tested. Electrical properties of powdered materials are determined on the basis of a set of the values for a set of parameters including quality factor (Q-factor), capacitance, dissipation factor, and dielectric permeability of the material. These parameter values can be related to such characteristics as moisture content, particle size, and material composition. The method and device can indicate the differences between the samples with various quantities of unwanted components or reaction products, and the extent of sample aging.

8 Claims, 17 Drawing Sheets

METHOD AND DEVICE FOR RAPID NON-DESTRUCTIVE QUALITY CONTROL OF POWDERED MATERIALS

CROSS-REFERENCE TO RELATED APPLICATIONS

Claims priority of Provisional Patent Application No. 61/124,984, Filed Apr. 21, 2008

FEDERALLY SPONSORED RESEARCH

None

SEQUENCE LISTING

None

FIELD OF THE INVENTION

The present invention relates to non-destructive testing for determination of electrical and associated properties such as composition, moisture content, and particle size, of bulk materials, and especially as related to the quality control of powdered materials such as cement.

BACKGROUND OF THE INVENTION

Physical and chemical properties of powdered materials may be critical parameters in a variety of industrial applications. Among many examples are the construction industry, wherein properties of cement have to be controlled, or the manufacture of lithium-based batteries where properties of the initial powdered electrode active materials must be tested, or in case of super capacitors and in other areas. General chemical analysis, if conducted for testing purposes, can consume a great deal of time and is often not practical for rapid quality control of powdered materials.

The main purpose of the present invention is to provide fast comprehensive non-destructive 100% quality control of powered materials of low conductivity, such as cement or cement-based composites, whether in a containers or on a moving conveyor-type line.

The invention may also be used for testing properties and for quality appraisal of powered materials that are used as active components in electrodes of chemical power sources such as lithium batteries, super capacitors, or as initial powdered components of solid electrolytes of power sources such as solid oxide fuel cell or thermal batteries.

The invention is based on the use of an electromagnetic method including an algorithmic procedure for processing informative signals, and devices for the non-destructive testing of powered compositions of dielectric materials, such as cement and related materials based on cement including stucco, grouts, and the like.

The resulting data represent the electrical properties of the powdered material. Electrical properties of powdered materials are determined on the basis of the values for a set of parameters including quality factor (Q-factor), capacitance, dissipation factor, and dielectric permeability of the material. Using appropriate calibration, these parameter values can be related to such characteristics as moisture content, particle size, and material composition.

The method and device allow determination and distinction between powdered material samples of adequate quality for a specific intended purpose ("Good" samples) and samples inadequate for that same specific intended purpose ("Bad" samples). The sensitivity and specificity of the present invention in this regard has been demonstrated, as describe below, by differentiating between powdered compositions comprised of various different ratios of "Good" and "Bad" materials in various samples compositions, thus indicating gradations of quality.

By this approach, it was demonstrated that the present invention was capable of distinguishing the differences between samples with various quantities of impurities or unwanted reaction products, and to determine the extent of sample degradation or aging.

Along with the development of the electronic and electromechanical device components and the software program for processing sensor signal information, a method for calibration was devised and applied for each type of powdered composition to be tested. This calibration routine is based on data points obtained from known "good" and "bad" samples of a given initial composition. The calibration data is provided to the signal processing program and is used by the program for interpreting the sensor signals obtained on "unknown" samples of the same type and intended composition. This allows for simplified measurements that are quite reliable.

BRIEF DESCRIPTION OF THE INVENTION

According to the present invention, the quality of powered materials such as various cement compositions (referred to simply as "cement" below) is determined, indirectly, by measuring the values of a set of electro-physical parameters through the use of an electromagnetic electrocapacitance method. The primary transducer (sensor) is a capacitor which may be designed in various forms, e.g. as two parallel plates, a hollow cylinder or as a coplanar capacitor. (The terms "transducer" and "sensor" will both be used in this application to refer to the components of a resonant circuit that are altered in their characteristics by direct contact with the powdered material being tested.)

Whatever the design of the capacitor, the entire surfaces of the electrodes of the primary capacitance sensor (transducer) come into contact with the powered material to be tested. Electrodes of the capacitor can be made of a suitable material such as copper foil.

One of the versions of the capacitor design can be as follows. A copper foil is glued to the interior surface of parallel plates of the dielectric transducer and is covered with varnish. In the case of a cylindrical capacitor, the copper foil is glued to the interior of the dielectric cylinder. The sensitive elements of the plate capacitor can be different by design.

Quality testing and control of powered materials may be performed manually, automatically, or in-line directly on the manufacturing line. Using the present invention, testing can be done by a powder manufacturer prior to shipment and by the powdered material end-user before final mixing and application of the material.

After initiation of the measurement, statistical data are automatically collected and summarized. According to the analysis program, the average numerical value of quality of the powder is determined by computation of sensor data compared with standards data. These data are stored in memory and displayed to the operator on suitable data display device (in this case, a liquid crystal display).

In accordance with the intended modes of operation of the invention, measurements are to be performed at various points, or in various regions, within the bulk powdered material mass. The data points thus obtained are integrated or averaged in the device. Each measurement is shown on the monitor, as well as the calculated average of the accumulated total number of measurements. The integrated output or summary of the data is displayed in the form of an indication as to the overall status or quality of the powdered material being tested.

The electromagnetic capacitance method of powder quality control involves placing the powder within the electric field of a capacitor and the determination of its properties based on the corresponding response of the electric field source. Powdered materials such as dry cements and cement compositions are essentially dielectrics. Therefore, the method employed provides for measurement of the dielectric properties of the materials. Data on the electromagnetic (dielectric) properties comprise the initial information for determining quality of the materials tested.

Dielectrics like cement have mainly bound charges, which form dipoles. Contained within powdered compositions of this kind there are various (sometimes unwanted) components such as moisture or acids. There are always free electric charges in these compositions, which create electric conductivity. Thus, in electric fields of powder-like composites there are currents caused by polarization, and conductivity currents. Overall, electrical currents found in such a system arise from various sources and are complex.

Various types of polarizations are known. For the invention presented here, consideration not only data on electric currents, but also of data on structural polarization is important. Structural polarization is an additional part of the mechanism that influences the relaxation. In particular, structural polarization is observed in moisture absorbing materials. Cement composites are active absorbers of moisture. In addition, they contain components that are acidic or readily react to form acids in the presence of water or carbon dioxide.

Cement-based composition quality depends, to a great extent, on the amount of moisture absorbed, the presence of acidic compounds, and the deviation of the percentages of components from their intended or standard proportions in the mixture. In an electromagnetic field, the total current density in powdered materials equals the sum of the conductivity current and polarization current densities.

When the effects of electromagnetic fields the total density of currents in powdered materials equals the amount of density of conductivity current and currents of shift. The following equation can be written for total density of currents:

$$J = J_{cond.} + J_{displ.moment} + J_{displ.polar.} \quad (1)$$

Where:
$J_{cond.}$ Is the conductivity current density?
$J_{displ.moment.}$ is the capacitance displacement current density,
$J_{displ.polar.}$ is the density of polarization displacement current.

The density of the capacitance current and density of polarization current depend on the frequency of the electric field used to drive the transducer.

Equation (2) shows that component values are dependent on the frequency.

$$J_{displ.moment} + J_{displ.polar} = j\omega\varepsilon_0\varepsilon'_\infty E + j\omega\varepsilon_0 \sum \frac{\Delta\varepsilon_i}{1 + j\omega\tau_i}; \quad (2)$$

where $\omega = 2\pi f$.

Due to losses caused by friction of polarized particles, polarized current surpasses (exceeds) the voltage of the capacitor electric field at angles less than 90° Therefore polarized current needs to be divided into two parts (components), which correspond, accordingly, to conductivity current and capacitance current. For that reason, total current density and its active and reactive components, are considered in the analysis of the present invention.

From the above discussion, let us consider how complex dielectric permeability depends upon complex conductivity:

$$\tilde{\varepsilon} = \varepsilon' - j\varepsilon'' = \frac{\tilde{\sigma}}{j\omega\varepsilon_0}, \quad (3)$$

and accordingly, the dependence between the real and imaginary components is:

$$\sigma' = \omega\in_0\in'' \text{ and } \sigma'' = \omega\in_0\in' \quad (4)$$

Material dielectric permeability $\in'$ characterizes the charge density on plates of the transducer, i.e. the degree of polarization and number of dipoles. The number of dipoles depends upon the amount of foreign particles.

The imaginary component $\in''$, i.e. dielectric permeability, characterizes losses related at a given frequency f in a powder-like material tested. Such losses are caused by both the increased conductivity and the friction experienced by polarized particles of foreign matter.

In addition to the above informative parameters, it is convenient to consider the dielectric losses tangent to the dielectric disposition:

$$tg\delta = \frac{\varepsilon''}{\varepsilon'}; \quad (5)$$

or as another parameter, the Q-factor of powder-like materials such as cement for building purposes.

$$Q = \frac{1}{tg\delta} = \frac{\varepsilon'}{\varepsilon''}; \quad (6)$$

The above theoretical analysis of the method of the present invention suggests that one should choose and optimize informative parameters as employed in the invention. Accordingly and as set forth in claims 2, 4, 5 and 6, below, the following should be done for each kind of material tested:
  Conduct research and choose an optimal frequency (f) for measurements
  Measure and analyze informative parameters:
    $\in'$ (or dielectric permeability, $\in$),
    tg δ, dielectric disposition
    losses in terms of Q-factor Q, and
  Select the test mode that utilizes the most effective parameters for a given sample.

Results and conclusions from the research carried out to reduce to practice, develop and test the present invention are shown in the Examples provided below.

DETAILED DESCRIPTION OF THE INVENTION

Prior to testing to determine the quality of powdered materials, laboratory standard samples of the materials must be prepared. For example, standards samples of cement-based compositions of good quality, as well as samples containing component quantities that deviate from the standards, are required. The components chosen for testing have to be those that determine the quality of materials, that is, those that significantly affect the quality of the materials tested. The total number of samples for each type of material to be tested should no less than nine. These sample data are used for construction of quality diagrams, look-up tables, or calibration curves to be used in calibrating and interpreting the data obtained from test measurements.

Samples of materials are tested following the method of non-destructive quality control described in the present invention. The quality of the material is determined on the basis and the results of measurements, as compared with the collected calibration data.

Just prior to testing, a powder such as cement is placed on a special pallet or is tested directly in its transport container. To obtain a comprehensive quality evaluation, cement samples are taken from different depths in the container or the bulk material. Before being tested the powdered materials are well mixed in the transport container.

The capacitance primary multi-sectional transducer, in general, may contain a number of alternating electrodes. Some of the electrodes are at potential, and others are grounded. On both sides of each electrode at potential there are grounded electrodes of identical forms. This allows locating the electric field of each potential electrode within the range of its adjacent sections. An adjustable frequency signal generator is used to drive the sensor.

Prior to testing, measuring is made, without powdered materials, of the following:
sensor capacitance—$C_0$ and
Q-factor of the resonance circuit, $Q_0$, with the capacitance sensor being a component of the (self) resonant system.

Figure 15:
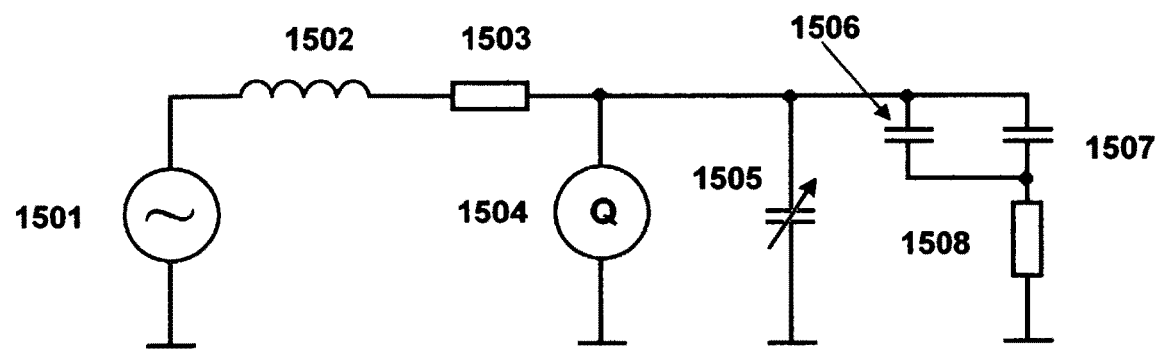
FIG. 15 shows the image of a equivalent measuring circuit: 1501 is the signal generator for the AC signal used; 1502 is the inductance coil L; 1503 is the resistor $r_L$ representing the resistive loss in the inductance coil; 1504 is the device for Q-factor measurement; 1505 is a variable capacitance; 1506 is the self-capacitance $C_0$ of the working sensor; 1507 is the added capacitance $C_d$ of the filled working sensor due to the effect of the of dielectric permittivity of the dry powder; and 1508 is the resistor $r_d$ representing the dielectric losses in the dry powder.

The value of Q-factor of resonance circuit is described by equation (7):

$$Q_0 = \frac{L}{C_0 r_L}, \quad (7)$$

where:
L is the circuit inductance (FIG. 15), $C_0$ is the capacitance sensor self-capacitance, $r_L$ is the inductive impedance of the coil. or resistance of real losses of inductance coil).

After measures of Co and Qo are made, the transducer is placed on the surface of the powdered material to be tested. Then an impulse generator is turned on. The generator supplies power to a coil of a vibrating electromagnetic acoustic transducer, which is assembled (joined) with a capacitance sensor as one equipment unit. The vibrating electromagnetic acoustic transducer has a constant magnet, a flat coil and a coil case made of polyurethane. Due to interaction of the magnetic field and the coil field, a Lorentz effect occurs. The Lorentz effect causes the capacitance sensor to vibrate at the ultrasound frequency. Then the sensor is lowered inside the powder-like material at a certain depth determined by an auxiliary capacitance sensor. The coplanar plates of the auxiliary capacitance sensor, in the form of thin band stripes, are located on the interior of the case for the working capacitance sensor, over its lower working end.

When the working volume of the transducer is filled up with powder, the capacitance of the auxiliary sensor will reach a certain predetermined (threshold) level. Exceeding this level of the capacitance serves to generate a signal that stops the vibration. Then the values of phase and frequency shifts in the sensor signals are recorded, which mean that the sensor is full of powder (has been fully plunged into powdered material). Vertical openings in the upper parts of the plates of the working capacitance sensor allow uniform powder density in each sensor capacitance area.

The Q-factor of the capacitive transducer which immersed in the powdered material is determined by equation (8):

$$Q_1 = \frac{L}{(C_0 + C_d)(r_L + r_d)}, \quad (8)$$

where:
$C_d$ is the added capacitance of the sensor, which is caused by the influence on the field of the transducer and the dielectric permeability of the powder tested. (FIG. 15)
$r_d$ is the resistance or dielectric losses in a tested powder.

The relative change of sensor Q-factor can be expressed on the basis of equations (7) and (8) as:

$$Q_r = \frac{\Delta Q}{Q_0} = \frac{C_0 r_d + C_d (r_L + r_d)}{(C_0 + C_d)(r_L + r_d)}. \quad (9)$$

In the case when Cd is lower, the sensor self-capacitance Co and $r_d$ and $r_L$ are of the same order such as in the case of dry powder cement (see examples below where these conditions are present), $Q_r$ is expressed as:

$$Q_r = \frac{r_d}{r_L + r_d}, \quad (10)$$

Since $r_L$ is a constant value, $Q_K$ is determined by the value of dielectric losses of dry powder ($r_d$). This is easily supported by experimental dependency of relative Q-factor on frequency for samples of cement-based powders of different quality as shown below.

The present invention provides a method of quality control for powdered materials, which are normally stored in an ordinary manufacturing environment. In such situations, it is always important to take into consideration the effect of humidity. Increasing moisture in cement-based materials leads to increased sensor capacitance due to the high dielectric permeability of water. Therefore, the Q-factor of the transducer is lowered because of the greater amount of moisture and straightforward conductivity on the surface of moistened grains of the powdered materials.

Figure 16:
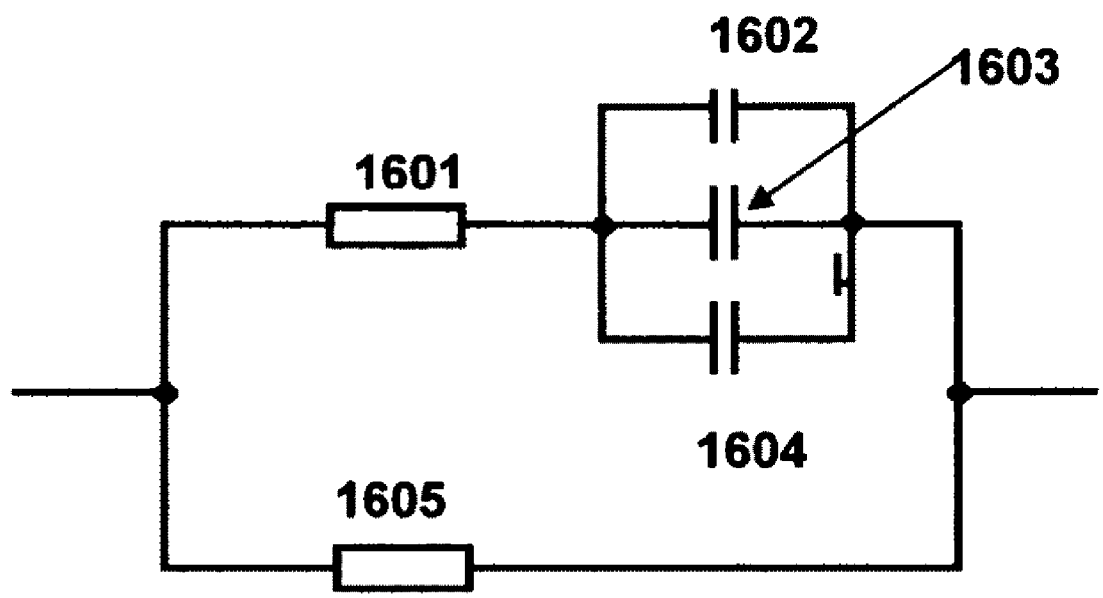
FIG. 16. shows a diagram of electrical equivalent circuit of the working sensor filled with powder. 1601 is the resistor $r_d$ representing dielectric losses in the dry powder, 1602 is the self-capacitance $C_0$ of the working sensor, 1603 is the added capacitance $C_d$ of the filled working sensor due to influence of dielectric permittivity of dry powder, 1604 is the added capacitance $C_h$ of filled working sensor due to influence of the moisture content of the powder, 1605 is the resistor $r_h$ representing the effect of the moisture content of the powder.

An equivalent scheme for a capacitive sensor for this particular case is presented in FIG. 16. Sensor impedance is computed by the following equation (11)

$$Z = \frac{\left(r_d + \frac{1}{j\varpi C}\right) \cdot r_h}{r_d + \frac{1}{j\varpi C} + r_h}, \quad (11)$$

where:
$C = C_0 + C_d + C_h$,
$C_h$ describes the increase in sensor capacitance caused by moisture effect,
$r_h$ is the conductivity of powdered material due to moisture.
If we separate the real and imaginary parts in Equation 5 we will obtain the following:

$$Z = \frac{r_h[1 + \varpi^2 C^2 r_d (r_d + r_h)]}{1 + \varpi^2 C^2 (r_d + r_h)^2} - j \frac{\varpi C r_h^2}{1 + \varpi^2 C^2 (r_d + r_h)^2} \quad (12)$$

Dividing the real component of complex impedance by the imaginary component we will obtain cotangent of the phase angle:

$$|ctg\varphi| = \frac{1 + \varpi^2 C^2 r_d (r_d + r_h)}{\varpi C r_h}. \quad (13)$$

Let us consider the value of product $A = \omega C r_h = \omega (C_0 + C_d + C_h) r_h$. The frequency of measurements ω, capacitance $C_0$ and $C_d$ are constant values. Capacitance $C_h$ increases when moisture rises. Resistance $r_h$ decreases with increased moisture. Within certain values of moisture, the value of the product residual is constant. Beyond the limits of those values, the A value can be graded on the basis of condenser capacitance of the condenser (transducer) filled with powder.

Condenser capacitance of the condenser filled with powder is determined after testing has been made on the data on the basis of frequency applying Thompson's equation. In this way the value of correctional signal A can be obtained.

When the term A is used in equation (13) we will get the following:

$$|ctg\varphi| = \frac{1 + \varpi^2 C^2 r_d^2 + A\varpi C r_d}{A}. \quad (14)$$

In equation (14) each value, except $r_d$, is obtained by measurement. The value of the resistance, therefore, can be computed from equation (14). This resistance describes dielectric losses on grains of powdered materials and is a part of the informative parameter Q signal. By the value of such an informative signal, and on the basis of data from the calibration curve or look-up table, we can obtain values that describe quality of powdered material tested.

If we take into account that the resistance $r_h$, under conditions of low humidity, significantly exceeds $r_d$ then the expression (8) can be simplified to the following:

$$|ctg\varphi| = \frac{1 + r_d \cdot A\varpi C}{A}. \quad (15)$$

After the first measurement, the sensor comes up to the surface of the powdered material. Then vibration is turned on for cleaning of electrodes of the sensor of residual powder. Sometimes powder may cling on the electrode surface. For thorough electrode cleaning, the vibration can require several more seconds. The cleaning process is regulated according to Q-factor values of the resonance circuit, together with the capacitive sensor. When Q-factor approaches the predetermined level or threshold, vibration stops.

This threshold value of the Q-factor of the resonance circuit, together with the capacitive sensor is set as equal to its unloaded Q-factor. The value of self Q-factor is set at the moment before first "plunging" of the sensor into powdered material. At the same moment an adjustment can be made, which depends upon the physical properties of the powdered material. Such an adjustment is chosen within 5% of resonance circuit Q-factor; it varies because of powder properties. Thus, the threshold value equals the unloaded (no powder) circuit Q-factor minus an adjustment value.

Figure 17:
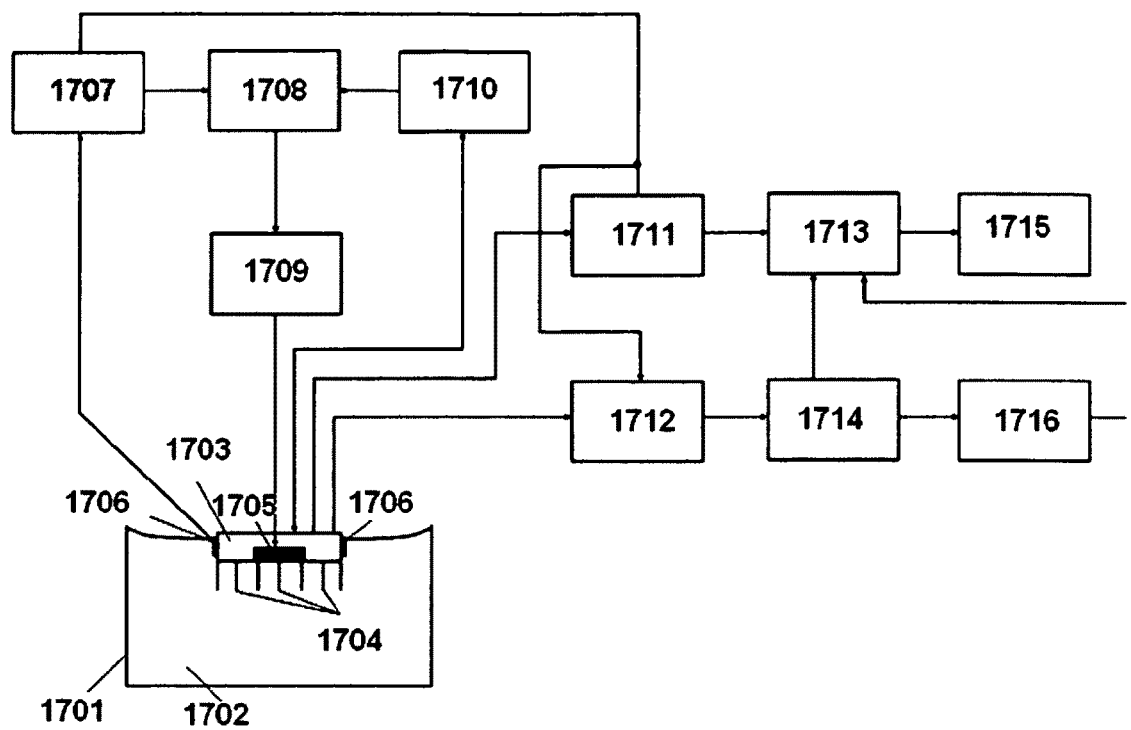
FIG. 17. is a block diagram of the measuring device wherein 1701 is the powder reservoir, 1702 is the powder, 1703 is the sensor case, 1704 are potential measuring electrodes, 1705 is the electromagnetic acoustic transducer, 1706 is the powder level sensor, 1707 is the capacitance of the powder level sensor measuring unit, 1708 is the control unit, 1709 is the pulse generator, 1710 is the signal generator, self-capacitance and Q-factor measuring unit, 1711 is the phase measuring unit, 1712 is the frequency measuring unit, 1713 is the circuit that generates the informative signal, 1714 is the capacitance of the "filled sensor" determination unit, 1715 is the classification unit, and 1716 is the circuitry for determining the correction signal required.

After capacitive electrode cleaning, repeated measurements are carried out in various areas of powdered material in the same container. Then average values are computed. The total number of measurements should be no less than nine. The quality of powdered material is evaluated by the averaged value of informative signals obtained from all measurements. An operational diagram of the equipment for control of powdered material quality is presented in FIG. 17.

The equipment consists of a sectional capacitive sensor of periodic structure with alternating "at potential" and grounded electrodes, a vibration electromagnetic acoustic transducer made as one unit with a capacitive sensor and mounted in the same case, and an auxiliary capacitive sensor with coplanar electrodes placed on side walls of the case of the working capacitive sensor.

An inductance coil together with the working capacitive sensor makes a resonance circuit. This resonance circuit is connected to a signal generator which is combined with a diaphragm for measuring sensor self capacitance and Q-factor of the resonant circuit in a single measuring device.

A generator driving the vibrating electromagnetic acoustic transducer transmits impulses to a flat inductance coil mounted in a polyurethane case. The circuit for measuring capacitance of an auxiliary capacitive sensor transmits command signals to the impulse generator diaphragm to stop vibration, and also to the circuits for measuring phase and frequency to record values of phase and frequency shifts, which correspond to a fully inserted or plunged sensor. The equipment also has a circuit for measuring the capacitance of the working sensor, which is fully submerged in powdered material, a circuit for processing incoming signals, a circuit for generating the informative signal, and a circuit for evaluating and indicating the quality of the of powdered material being tested.

EXAMPLES

The Examples described below are provided for illustration purposes only and are not intended to limit the scope of the invention.

Example 1

The cylindrical capacitive transducer has copper electrodes that are 70 mm×30 mm with a thickness of 10-20 µm. The electrodes are made as half-cylinders and mounted inside the lower part of the transducer case made of dielectric in a cylinder-like form. The diameter of the dielectric is 60 mm and the height is 70 mm. The thickness of the wall in the areas of electrodes is 1.00 mm. As an auxiliary induction for the circuit, a coil with a diameter of 18 mm, together with two wire coils with an outside diameter of 0.84 mm was connected to it is used.

Since the height of the entire cylindrical part of the capacitive transducer is commensurable with the entire height of the transducer $L_1$ and compatible with the height of the copper electrode $L_2$ the capacitance is described by the expression (16):

$$C = \frac{\varepsilon_0 \varepsilon_r L_2}{\pi} \ln \frac{\sin\left(\frac{\phi_3 - \phi_0}{2}\right)\sin\left(\frac{\phi_2 - \phi_1}{2}\right)}{\sin\left(\frac{\phi_2 - \phi_0}{2}\right)\sin\left(\frac{\phi_3 - \phi_1}{2}\right)}, \quad (16)$$

where:
$\in_0 = 8.854 \times 10^{-12}$,
$\in_r = \in' = 1$,
Φ—are the values of angles of electrode segment in a cylindrical co-ordinate system.

Capacitance values can be expressed in numbers as: C=1.81 pF.

The research described in Example 1 was conducted on the basis of two cement compositions: 584 and 795. There were two samples for each composition as described above, which were labeled as "good" and "bad". A Q-meter (HP) instrument and above described transducers were used for measurements. For capacitive transducers with capacitance values computed by equation (1), and measurements of the Q-factor and capacitance were made over the frequency range of 12-70 MHz. On the basis of the measurements of capacitance and Q-factor, dielectric dissipation and dielectric permeability values were computed.

Table 1 describes the following parameters:
f=frequency in MHz
$Q_{0-}$=Q-factor prior to placing a tested cement powder into the transducer
$C_0$=capacitance prior to placing a tested sample into the transducer $Q_{1\_}$=Q-factor after placing a tested sample into the transducer $C_1$=capacitance after placing a tested sample into the transducer $\epsilon \times 10^{-3}$ dielectric permeability of the tested powder tg $\delta \times 10^{-3}$—dielectric dissipation of the sample being tested.

TABLE 1

Effect of electric field frequency on capacitance values, Q-factor, and computed values of dielectric permeability and dissipation factor for cement-based composite 584.

| No | F | $Q_0$ | $C_0$ | $Q_1$ | $C_1$ | $\epsilon \times 10^{-3}$ | tg$\delta \times 10^{-3}$ |
|----|----|-----|-------|-----|------|----------|----------|
| 1  | 12 | 93  | 420.5 | 91  | 419.5 | 2.37  | 99.37 |
| 2  | 15 | 100 | 268   | 99  | 267   | 3.73  | 27.07 |
| 3  | 20 | 113 | 148   | 110 | 146   | 13.5  | 17.86 |
| 4  | 25 | 123 | 91.4  | 118 | 90    | 15.3  | 22.49 |
| 5  | 35 | 144 | 43.5  | 132 | 42    | 34.48 | 18.3  |
| 6  | 45 | 160 | 22.8  | 139 | 21.9  | 39.5  | 13.46 |
| 7  | 70 | 231 | 21.5  | 201 | 20.5  | 46.5  | 13.89 |
| 8  | 12 | 91  | 421.5 | 90  | 420   | 3.56  | 34.31 |
| 9  | 15 | 100 | 268   | 98  | 268   |       |       |
| 10 | 20 | 113 | 148   | 109 | 147   | 6.76  | 48.06 |
| 11 | 25 | 123 | 91.5  | 117 | 90    | 16.4  | 25.43 |
| 12 | 35 | 143 | 43.5  | 134 | 42    | 34.48 | 13.62 |
| 13 | 45 | 159 | 22.9  | 142 | 21.9  | 43.67 | 17.24 |
| 14 | 70 | 231 | 21.5  | 194 | 20.5  | 60.46 | 17.75 |

Numbers 1-7 correspond to the "good" sample and number 8-14 correspond to the "bad" sample.

Values for the parameters and tg δ are computed by equations:

$$\varepsilon = \frac{C_0 - C_1}{C_1}; \quad (17)$$

$$tg\delta = \frac{(Q_0 - Q_1)C_0}{Q_0 Q_1 (C_0 - C_1)}. \quad (18)$$

Figure 1:
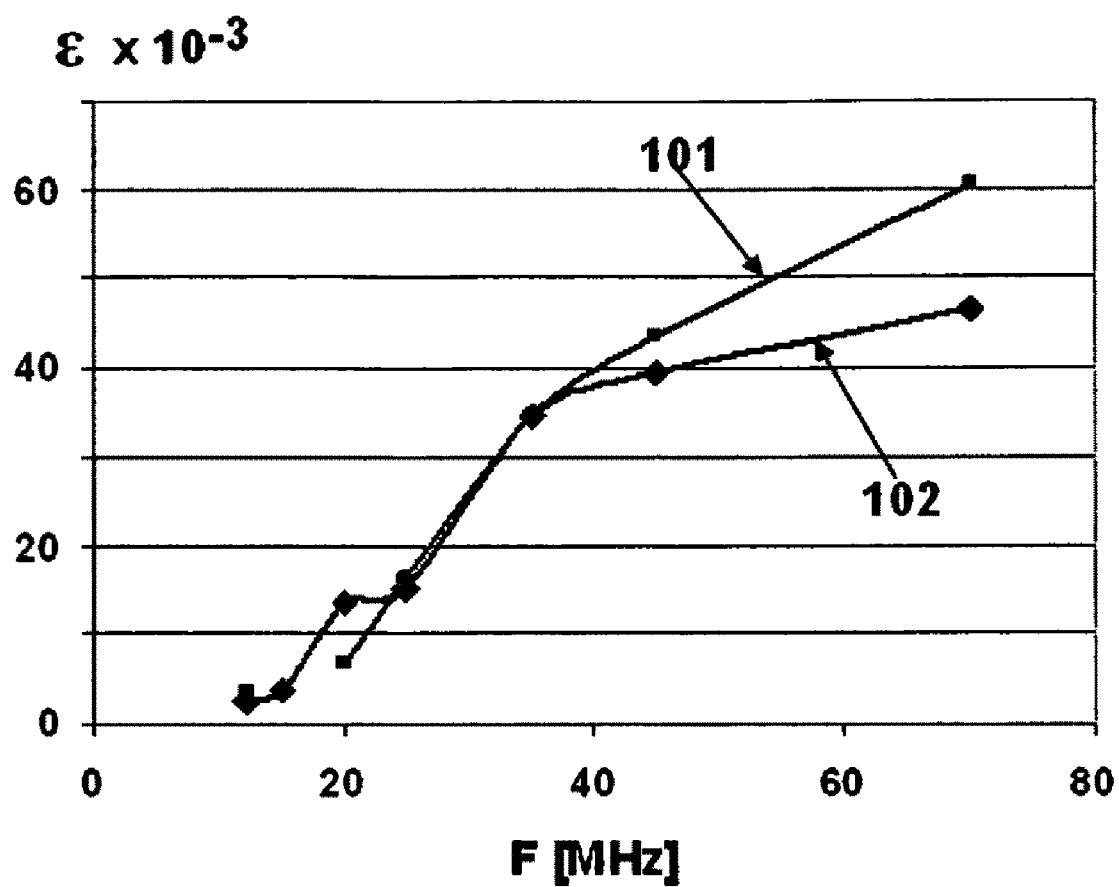
FIG. 1 illustrates the dielectric permeability ($\in$) as a function of frequency. As a test sample, the cement-based composition designated as "584" was used. The samples were given the following designations: 101 (bad sample); 102 (good sample). Measurements were carried out with a cylindrical primary transducer.
Figure 2:
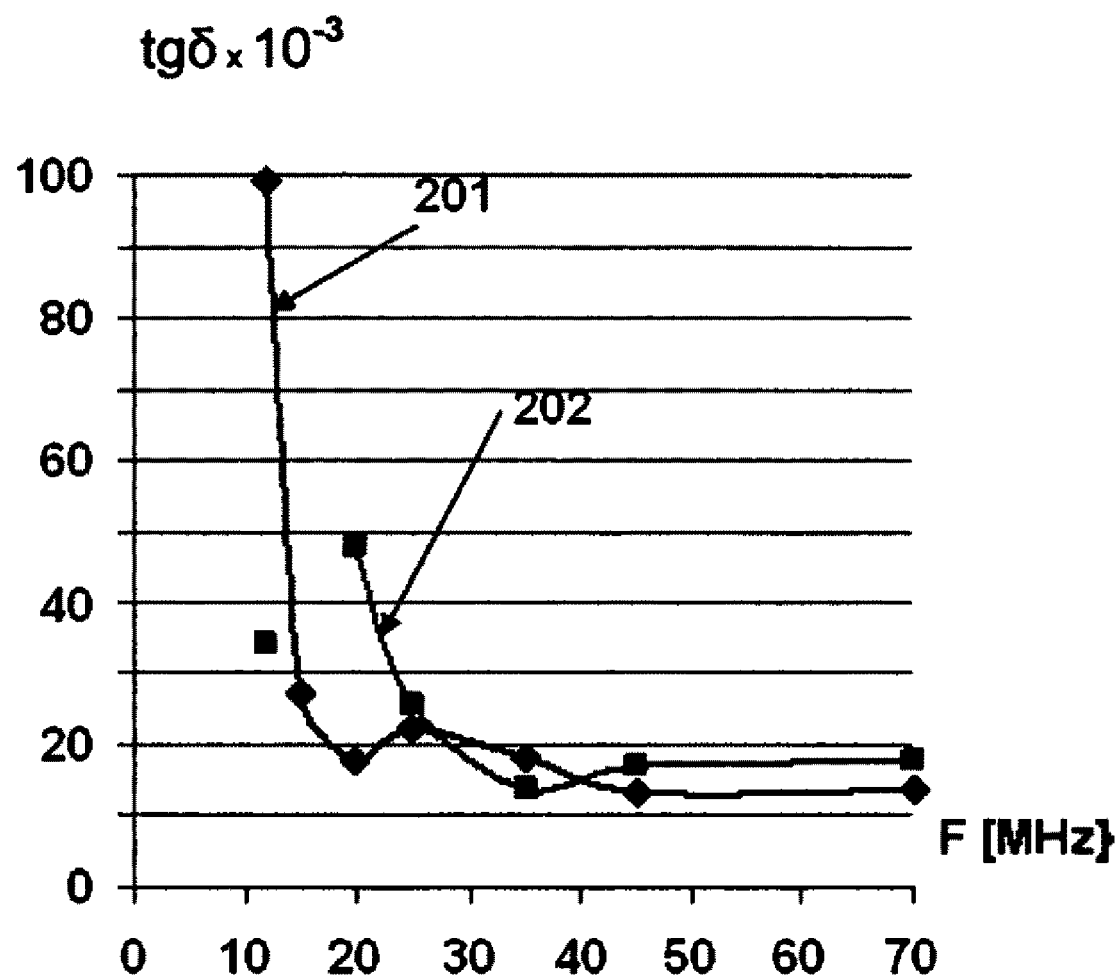
FIG. 2 illustrates the dissipation factor (tg δ) as a function of frequency. As a test sample, the cement-based composition 584 was used. The samples were given the following designations: 201 (bad sample); 202 (good sample). Measurements were carried out with a cylindrical primary transducer.
Figure 3:
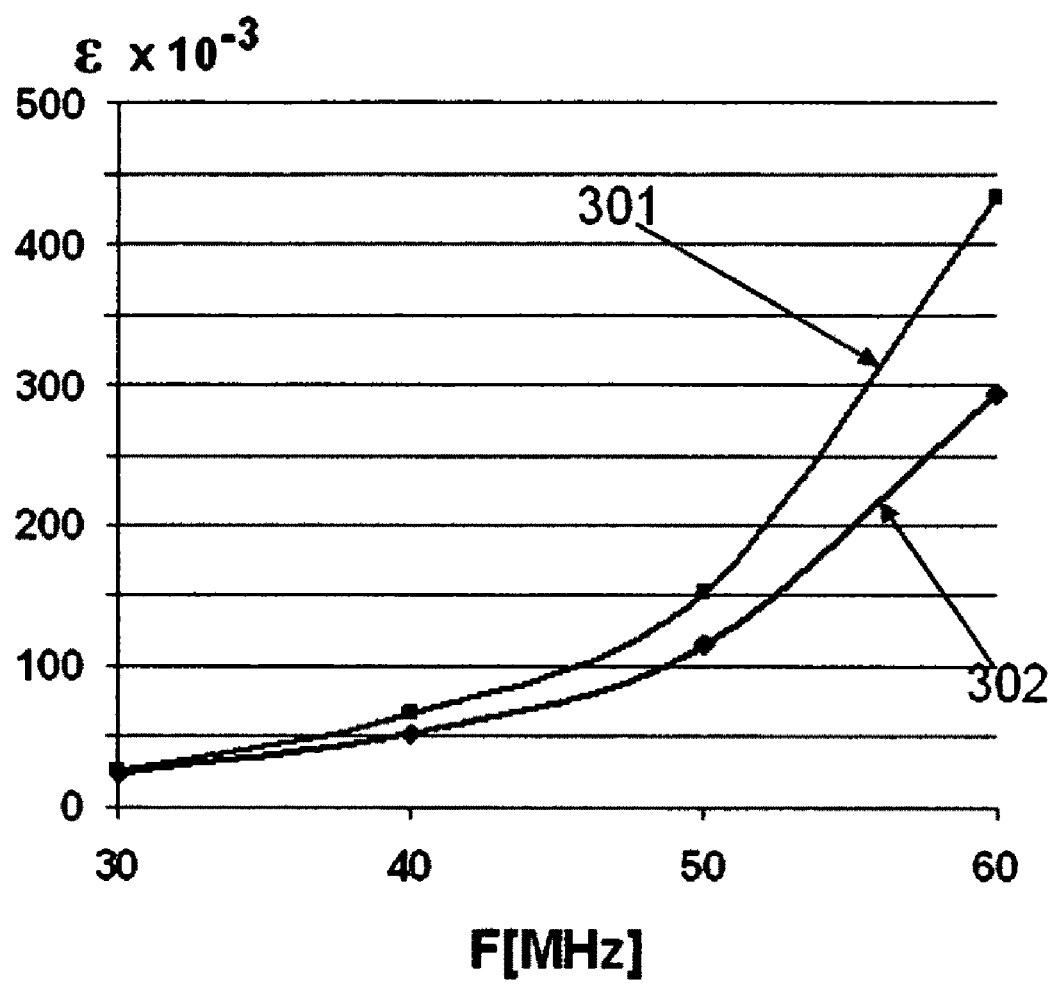
FIG. 3 illustrates the dielectric permeability (∈) as a function of frequency. As a test sample, the cement-based composite 584 was used. The samples were given the following designations: 301 (bad sample); 302 (good sample). Measurements were carried out with a primary transducer made of parallel flat electrodes.
Figure 4:
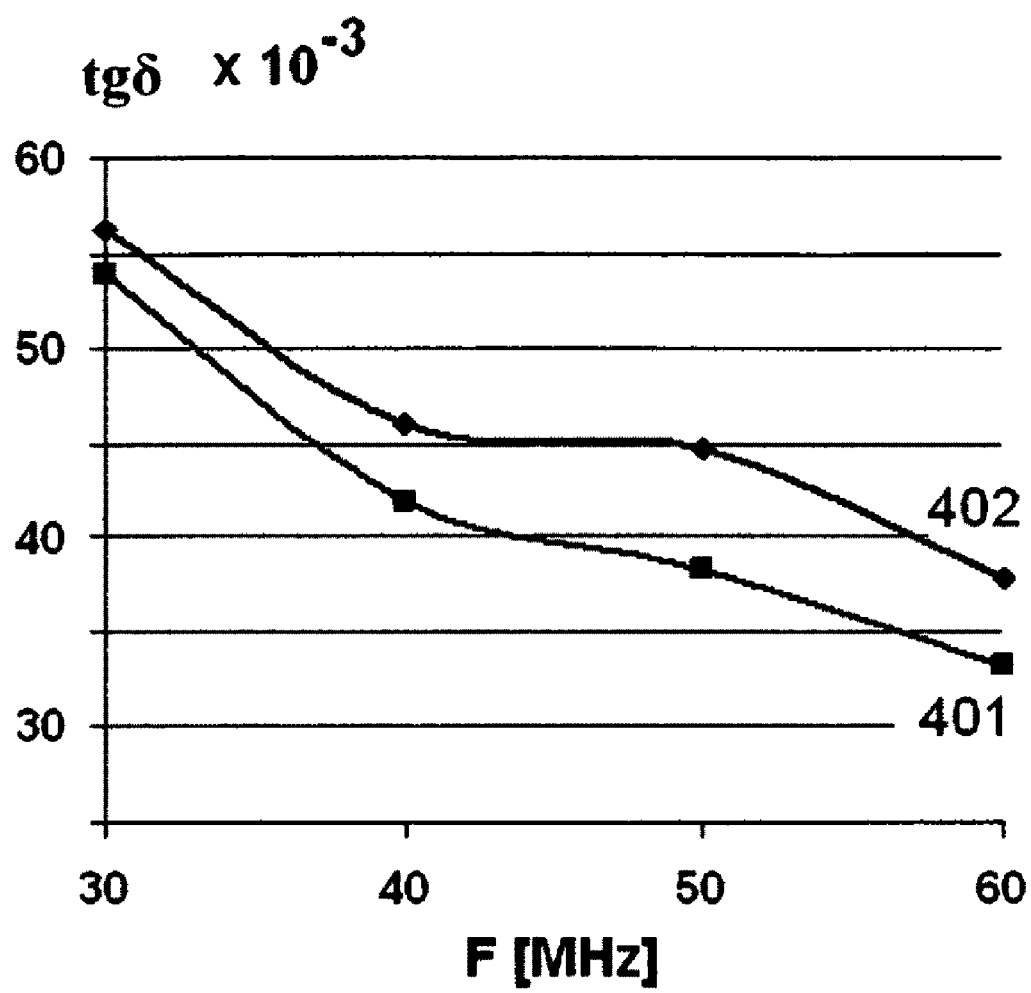
FIG. 4 illustrates the dissipation factor (tg δ) as a function of frequency. As a test sample, the cement-based composition designated as 584 was used. The samples were given the following designations: 401 (bad sample); 402 (good sample). Measurements were carried out with a primary transducer made of parallel flat electrodes.
Figure 5:
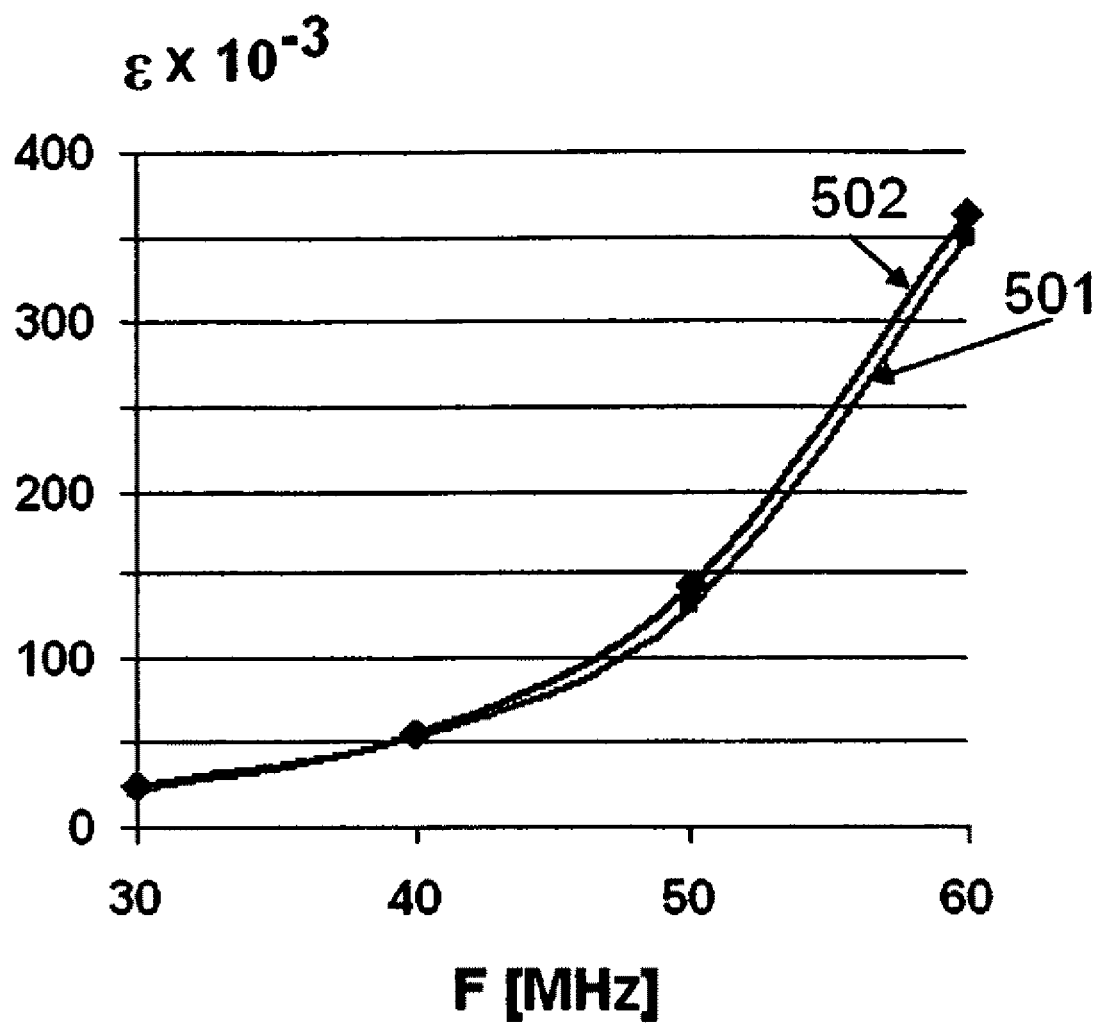
FIG. 5 illustrates dielectric permeability as a function of frequency. As a test sample, the cement-based composition designated as "795" was used. The samples were given the following designations: 501 (bad sample); 502 (good sample). Measurements were carried out with a primary transducer made of parallel flat electrodes.
Figure 6:
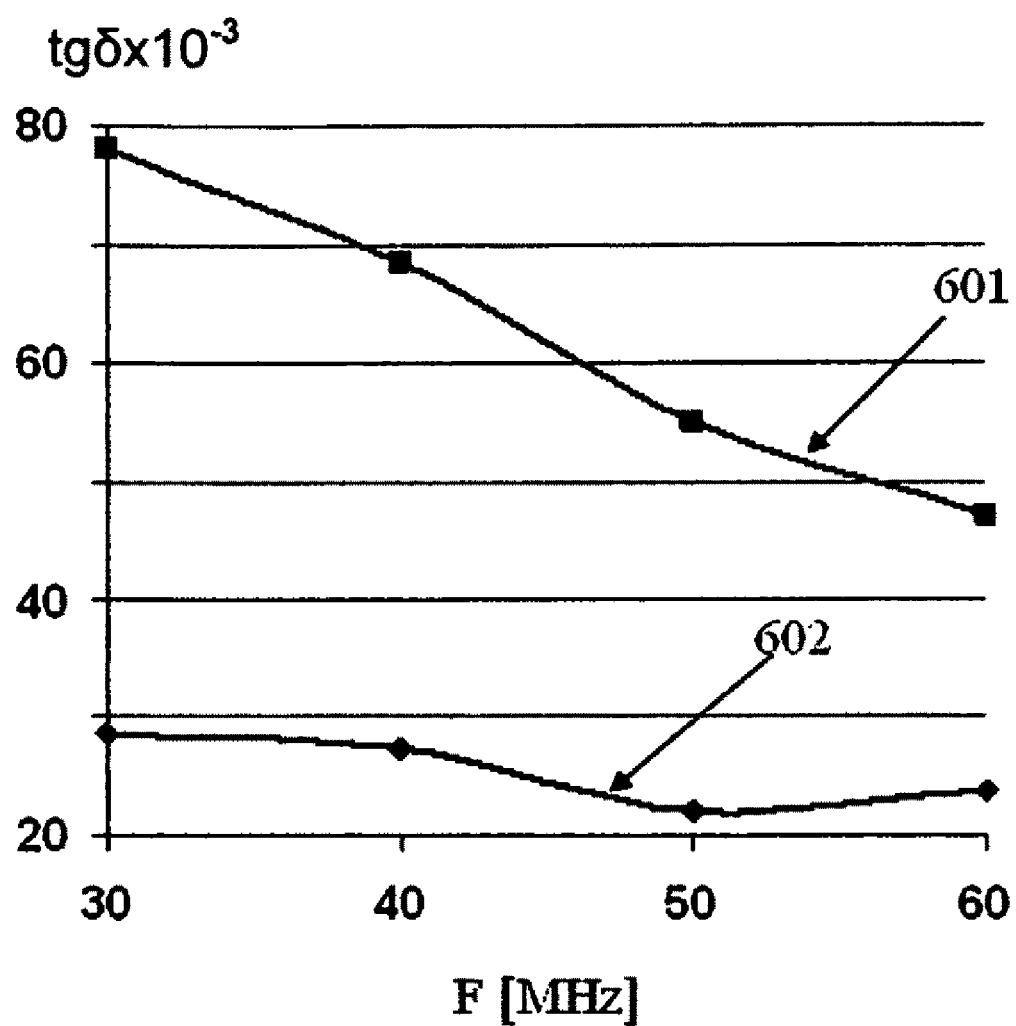
FIG. 6 illustrates dissipation factor (tg δ) as a function of frequency. As a test sample, the cement-based composition 795 was used. The samples were given the following designations: 601 (bad sample); 602 (good sample). Measurements were carried out with a primary transducer made of parallel flat electrodes.

FIGS. 1 and 2 illustrate the measured dielectric permeability and dissipation factor of a tested powder as a function electric field frequency. Parameter values in Table 1 and diagrams 101 and 102 in FIG. 1 suggest that cylindrical transducers are better used in the frequency range above 55 MHz. In the case of lower frequencies, the parameter of dielectric permeability does not provide adequate information for quality control of certain samples.

Analysis of data on dielectric dissipation from Table 1 and diagrams 201 and 202 in FIG. 2 shows that the transducer design in question cannot be used for control using the dielectric dissipation parameter (tg δ) in all frequency ranges. Differences between the obtained values of this parameter are within the method error range.

Example 2

A capacitive transducer is made of two parallel electrodes of copper foil of size 120 mm×30 mm with a thickness of 20 microns. Electrodes are placed inside the lower part of dielectric transducer case. The distance between the electrodes is 4 mm. The thickness of dielectric wall in the area of electrodes is 1 mm. In the case when the total area of condenser parallel plates is large, such that the electric field distorting effect can be ignored on the plate edges, Gauss's law was applied:

$$C = \epsilon_0 \epsilon' S/d = 8.854 \times 10^{-12} \times \epsilon' S/d = 7.969 \text{ pF}, \quad (19)$$

In this case, transducer capacitance is higher as compared with the cylindrical transducers in Example 1. The increased capacitance as compared with Example 1 allows increased sensitivity. Measurements were made by the instrument described in Example 1. The same samples of cement-based compositions were used.

The results of measurements are presented in Table 2. On the basis of these data diagrams were drawn (FIG. 3-6), which illustrates the dependence of the measured and computed parameters upon frequency.

In Table 2: samples 1-4 and 9-12 were "good" cement-based compositions 584 and 795 and samples 5-8 and 13-16 were "bad" cement-based compositions 584, 795

Analysis of data on parameters in Table 2 and diagrams in FIGS. 3-6 suggests that it is better to use a capacitive transducer with parallel flat electrodes, and not consider the dielectric dissipation parameter, but look at the relative change of Q-factor, which can be computed by the following equation:

$$Q_{relative} = \frac{Q_0 - Q_1}{Q_0}. \quad (20)$$

TABLE 2

Measured capacitance values, Q-factor, and computed values of dielectric permeability and dissipation factor of the test powder as a function of frequency in the range 30-60 MHz.

| No | F MHz | $Q_0$ | $C_0$ | $Q_1$ | $C_1$ | $\epsilon 10^{-3}$ | tg$\delta 10^{-3}$ |
|----|-----|-------|--------|-------|--------|-------|-------|
| 1 584, good | 30 | 111 | 273.02 | 97 | 266.7 | 23.15 | 56.2 |
| 2 584, good | 40 | 135 | 147.5 | 102 | 139.8 | 52.2 | 45.9 |
| 3 584, good | 50 | 161 | 88.3 | 88 | 78.1 | 115.5 | 44.6 |
| 4 584, good | 60 | 180 | 53.4 | 60 | 37.7 | 294 | 37.8 |
| 5 584 bad | 30 | 111 | 272.45 | 96.3 | 265.5 | 25.5 | 53.9 |
| 6 584 bad | 40 | 135 | 147.42 | 98 | 137.6 | 66.6 | 41.98 |
| 7 584 bad | 50 | 160 | 87.93 | 82.8 | 74.55 | 152.2 | 38.3 |
| 8 584 bad | 60 | 179 | 53.25 | 50 | 30.18 | 433.2 | 33.26 |
| 9 795 good | 30 | 110.5 | 272.6 | 102 | 265.8 | 24.9 | 28.58 |
| 10 795 good | 40 | 135 | 147.15 | 112 | 138.98 | 55.5 | 27.4 |
| 11 795 good | 50 | 159.5 | 88.26 | 106 | 75.68 | 142.5 | 22.2 |
| 12 795 good | 60 | 178 | 53.4 | 70 | 33.96 | 364 | 23.8 |
| 13 795 bad | 30 | 110 | 271.71 | 92.5 | 265.72 | 22 | 78 |
| 14 795 bad | 40 | 134.5 | 146.7 | 91 | 138.75 | 54.2 | 68.4 |
| 15 795 bad | 50 | 158 | 87.72 | 74 | 76.26 | 130.6 | 54.99 |
| 16 795 bad | 60 | 175 | 52.9 | 45 | 34.41 | 349.5 | 47.2 |

Analysis of numbers in the above Tables 1 and 2 and diagrams shows that use of a capacitive transducer with parallel flat electrodes of the size described in Example 2 is problematic if an informative parameter of dielectric permeability is considered.

When a capacitive transducer with parallel flat electrodes was used it was found out that the small distance between electrodes makes it difficult to evenly fill the space between electrodes with powder. And it is also difficult to entirely remove the powder.

Example 3

Figure 7:
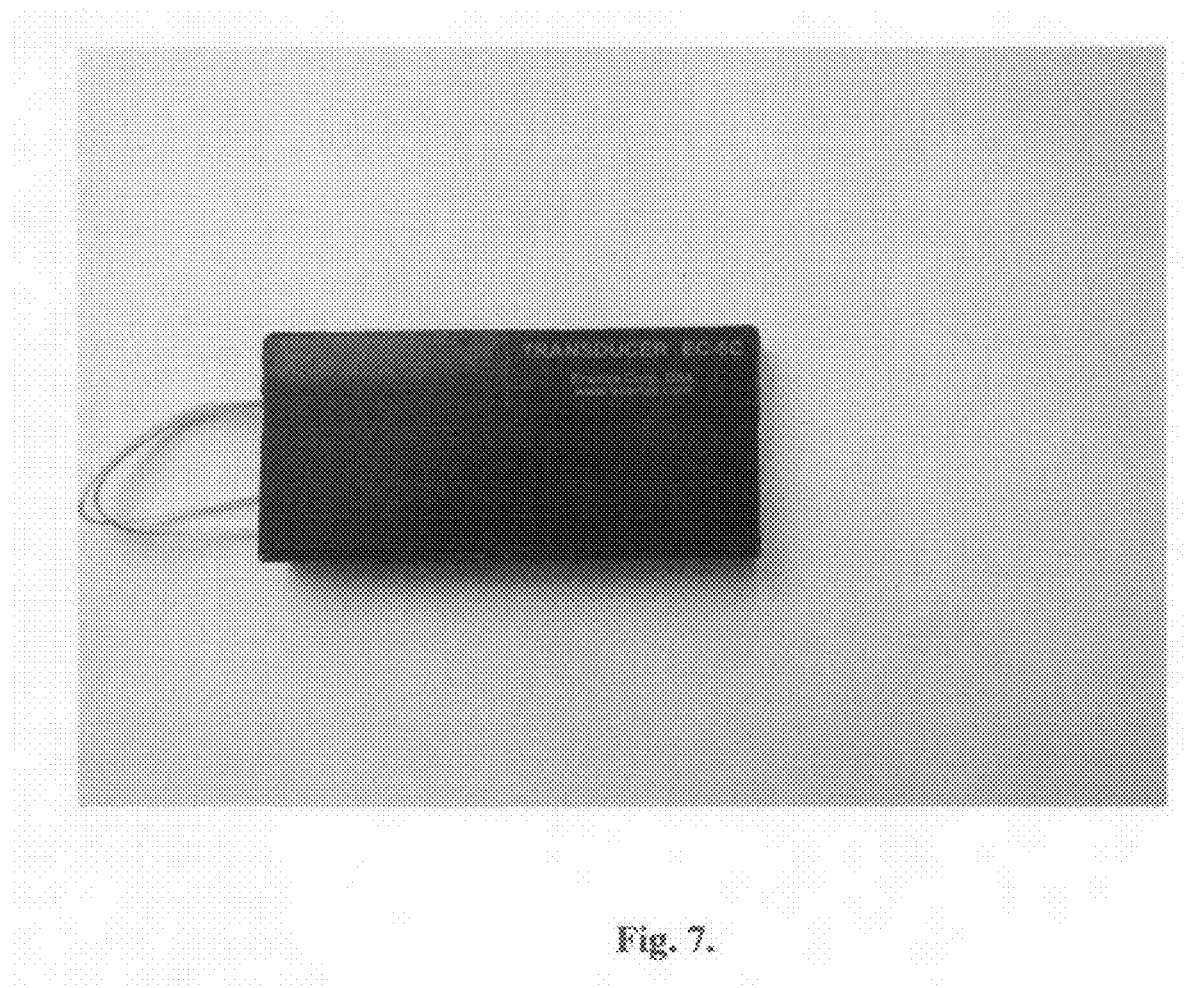
FIG. 7 shows the image of the primary capacitive transducer designated as "EC-5C".

In this example, results of powder testing using transducer EC-5C are shown (FIG. 7). The transducer has parallel flat electrodes of copper foil. Electrodes sizes are: a=100 mm, b=12.5 mm and thickness=15 microns. Electrodes are mounted inside the lower part of a transducer case. The case is made of dielectric. The thickness of the wall in the area of the electrodes is 1 mm. The distance between electrodes L is 7 mm. The increased distance between electrodes is needed to ensure even filling of the space between electrodes when a transducer is inserted into the powder being tested.

To compute capacitance of a capacitor with increased space between electrodes equations (6 and 7) were applied. The equation takes into account the distortion of the field at the capacitor edges caused by the electrodes plates.

$$C = 4\varepsilon a \frac{b}{l} + 0.5 C_0, \quad (21)$$

where;

$$C_0 \cong \frac{16 \varepsilon a}{\frac{a}{b} \text{arcsh} \frac{b}{a} + \text{arcsh} \frac{a}{b}}. \quad (22)$$

The resulting capacitance value is C=2.45 pF.

An experimental measurement of the transducer capacitance over the frequency range 24-70 MHz produced and average value C=2.15 pF with a total of 20 measurements. This proves that the formula is acceptable for computational purposes.

The transducer is installed on a stand that allows strictly vertical movement while the transducer is being inserted into the test powder material. In the measurement process, the space between electrodes is entirely filled with the same quantity of cement mixture. In Table 3 the results of Q-factor are shown after seven measurements of composition 795 at each frequency.

Calculations indicate that error in measurements is no more than 5-7%. To evaluate in quantitative terms the degree of powder quality deviation from standard, a higher sensitivity of the method employed is needed. These procedures are described below.

TABLE 3

Q-factor as a function of frequency and results of replicate measurements.

| | F | Serial number of a measurement | | | | | | | |
|---|---|---|---|---|---|---|---|---|---|
| # | MHz | 1 | 2 | 3 | 4 | 5 | 6 | 7 | Average |
| 1 | 30 | 49.5 | 49.5 | 49.2 | 51.9 | 75.0 | 53.9 | 54.7 | 54.8 |
| 2 | 40 | 100 | 104.8 | 103.2 | 103.9 | 121.0 | 111.6 | 105.7 | 107.2 |
| 3 | 50 | 178.9 | 180 | 176.5 | 177.2 | 197.3 | 184.2 | 178.9 | 181.9 |
| 4 | 60 | 272.2 | 269.7 | 269.2 | 273.9 | 300.9 | 285.7 | 265.9 | 276.8 |
| 5 | 70 | 384.2 | 393.6 | 382.2 | 392 | 401.7 | 406.3 | 394.6 | 393.5 |
| 6 | 30 | 107.6 | 108.9 | 99 | 99.5 | 107.1 | 104 | 110 | 105.2 |
| 7 | 40 | 204.0 | 201.6 | 194 | 193 | 204.2 | 187 | 204.9 | 198.4 |
| 8 | 50 | 315.6 | 320 | 284.8 | 294.9 | 317.2 | 300.7 | 314.3 | 306.8 |
| 9 | 60 | 441.3 | 466.7 | 413.9 | 424.7 | 451.9 | 431.8 | 454.3 | 440.7 |
| 10 | 70 | 571.8 | 574.5 | 567.4 | 563.3 | 592.0 | 594.9 | 592.4 | 579.5 |

The test powder is the cement-based composition 795. The powder being tested is placed between the electrodes of the capacitor.

Example 4

Figure 8:
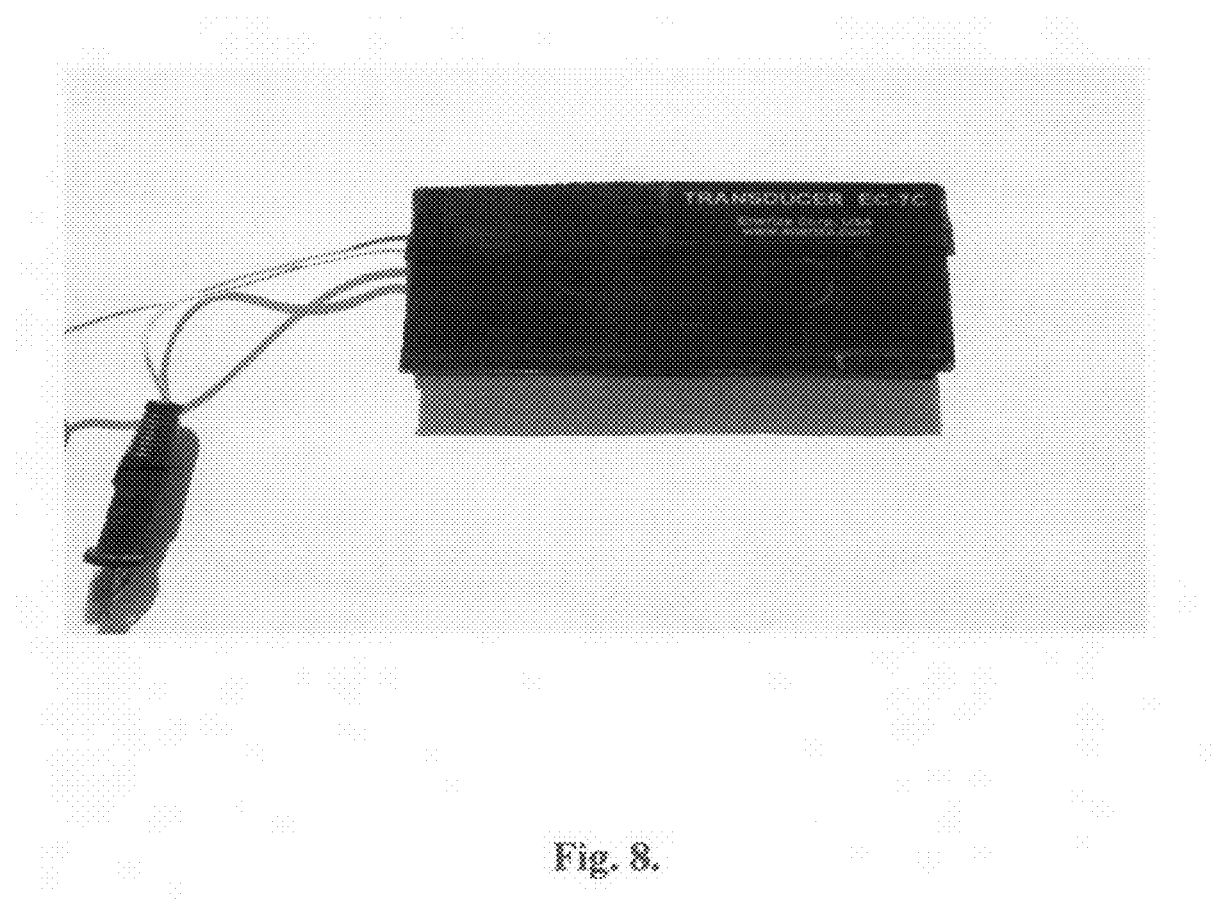
FIG. 8. shows the image the primary capacitive transducer designated "EC-7C".

Higher sensitivity of the method employed is attained thru increasing the capacitance of the transducer. Measurements were carried out by the use of transducer EC-7C (FIG. 8). The sizes of flat parallel copper electrodes were a—100 mm, b=30 mm and the thickness was 15 micron. The transducer capacitance computed according to equation (6) is C=5.01 pF.

Q-factor and the losses of the Q-factor ($Q_{relative}$) were accepted as an informative parameter in the process of testing of powdered materials when powder was placed in the space between the electrodes. Computations were made according to equation (5).

TABLE 4

Effect of frequency and of enlarged transducer capacitance on Q-Factor losses when the test powder was placed in the space between the electrodes of a capacitive transducer.

| # | F MHz | $Q_0$ | $C_0$ | $Q_1$ | $C_1$ | $Q_{relative}$ |
|---|---|---|---|---|---|---|
| | | | # 795$_{(EC-5C)}$ | | | |
| 1 | 24 | 87 | 453.3 | 78 | 441.9 | 103.4 |
| 2 | 30 | 100 | 287 | 82.9 | 275.6 | 171 |
| 3 | 40 | 120 | 155.7 | 81.4 | 142.4 | 321.7 |
| 4 | 50 | 143 | 94.2 | 67.5 | 76.5 | 528 |
| 5 | 60 | 163 | 58.5 | 43.2 | 31.35 | 735 |
| 6 | 24 | 86.6 | 452.4 | 79.5 | 441.9 | 81 |
| 7 | 30 | 99.1 | 287 | 87.1 | 275.3 | 120.1 |
| 8 | 40 | 119.8 | 155.7 | 90.8 | 142.4 | 242.1 |
| 9 | 50 | 141.5 | 94.2 | 77.8 | 76.45 | 450.2 |
| 10 | 60 | 160 | 58.7 | 56.2 | 32.1 | 648.7 |
| | | | # 795$_{(EC-7C)}$ | | | |
| 11 | 24 | 87.1 | 451.0 | 85.2 | 441.0 | 22.5 |
| 12 | 30 | 98.3 | 287.2 | 95 | 277.1 | 34.5 |
| 13 | 40 | 112.1 | 155.8 | 104.5 | 144.7 | 72.6 |
| 14 | 50 | 116.6 | 94.4 | 104 | 81 | 121.6 |
| 15 | 60 | 106.4 | 59.2 | 89 | 41.9 | 195.4 |
| 16 | 70 | 87.2 | 27.1 | 67.3 | 21.3 | 296.2 |
| 17 | 24 | 81.9 | 452.2 | 77.5 | 441.9 | 56.2 |
| 18 | 30 | 89.3 | 286.7 | 82 | 275.5 | 89.1 |
| 19 | 40 | 90.38 | 155.7 | 77.3 | 142.2 | 169.3 |
| 20 | 50 | 78.74 | 94.3 | 62 | 76.3 | 270 |
| 21 | 60 | 53.59 | 59.0 | 38.7 | 31.6 | 385 |
| 22 | 70 | 32.92 | 31.0 | 21.8 | 16.4 | 510 |

For the powder designated 795 transducers EC-5C and EC-7C were used. Data are presented in Table 4, No. 1-10 are from EC-5C and in Table 4, No. 11-18 are from EC-7C.

To find out if the test procedure can be performed over a wider frequency range, we also made measurements at low frequency range up to 100 KHz. Results of the measurements are presented in Table 5.

TABLE 5

$Q_{average}$ for samples 795 with different ratios between quantity of the "Good" and "Bad" materials.

| | Percentage of mixture | | | | | |
|---|---|---|---|---|---|---|
| # | BAD 100 | G/B 25:75 | G/B 50:50 | G/B 75:25 | GOOD 100 | Note |
| | | | 74.5 kHz | | | |
| 1 | 11 | 11.5 | 15 | 16.5 | 23.5 | |
| 2 | 11 | 11.5 | 13.5 | 16 | 23.5 | |
| 3 | 10 | 12.5 | 14.5 | 16 | 24 | |
| 4 | 11 | 11.5 | 14 | 16.3 | 25 | |
| 5 | 11 | 12 | 14.7 | 17 | 23.5 | |
| 6 | 11 | 12 | 14.2 | 16 | 24 | |
| | 10.83 | 11.83 | 14.32 | 16.3 | 23.92 | Average |
| | | | 90.0 kHz | | | |
| 1 | 13 | 16 | 19 | 24 | 30.2 | |
| 2 | 14.3 | 16 | 19.5 | 22.9 | 30 | |
| 3 | 14.3 | 14 | 19.5 | 24 | 30 | |
| 4 | 13 | 14 | 17 | 22 | 30.5 | |
| 5 | 14 | 15.5 | 19.5 | 23 | 28 | |

TABLE 5-continued

Q$_{average}$ for samples 795 with different ratios between quantity of the "Good" and "Bad" materials.

| | Percentage of mixture | | | | |
|---|---|---|---|---|---|
| # | BAD 100 | G/B 25:75 | G/B 50:50 | G/B 75:25 | GOOD 100 | Note |
| 6 | 14 | 14.8 | 18.6 | 22 | 29.8 | |
| | 13.77 | 15.05 | 18.85 | 22.98 | 29.75 | Average |

Figure 11:
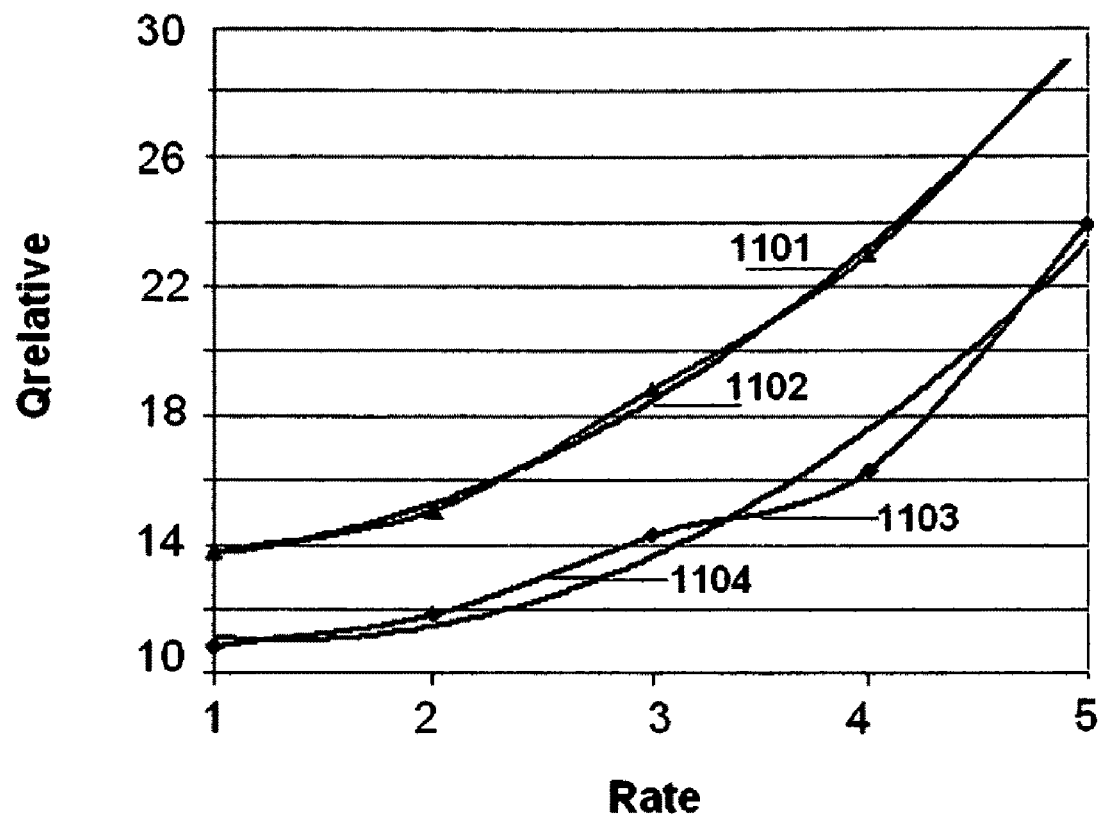
FIG. 11 illustrates results of non-destructive testing of "good" and "bad" samples of cement-based composition 795. The frequency of the measurement for 1101 was f=74.5 kHz; for 1104, it was f=90 kHz. 1102, 1103 show the charts are approximated by polynomials of the second degree with correlation coefficients as follows: for 1102, $R^2=0.9983$ and for 1103, $R^2=0.9754$. Measurements were carried out with the capacitive primary transducer EC-7C.

Table 5 and FIG. 11 contain results of evaluation of sample 795, including computed average values. Measurements were made at two frequencies; 74.5 kHz and 90 kHz. The graphs are approximated by polynomials of the second degree with correlation coefficient $R^2$=0.9983 and $R^2$=0.9754. One can notice precise recurrence of dependencies at both frequencies.

The results of the evaluation are presented in FIG. 11 and Table 5 and confirm that the method and transducers developed in accordance with the invention allow identification, with high level of accuracy, "Good" and "Bad" samples, as well as compositions comprised of various proportions of the original "Good" and "Bad" samples.

Figure 9:
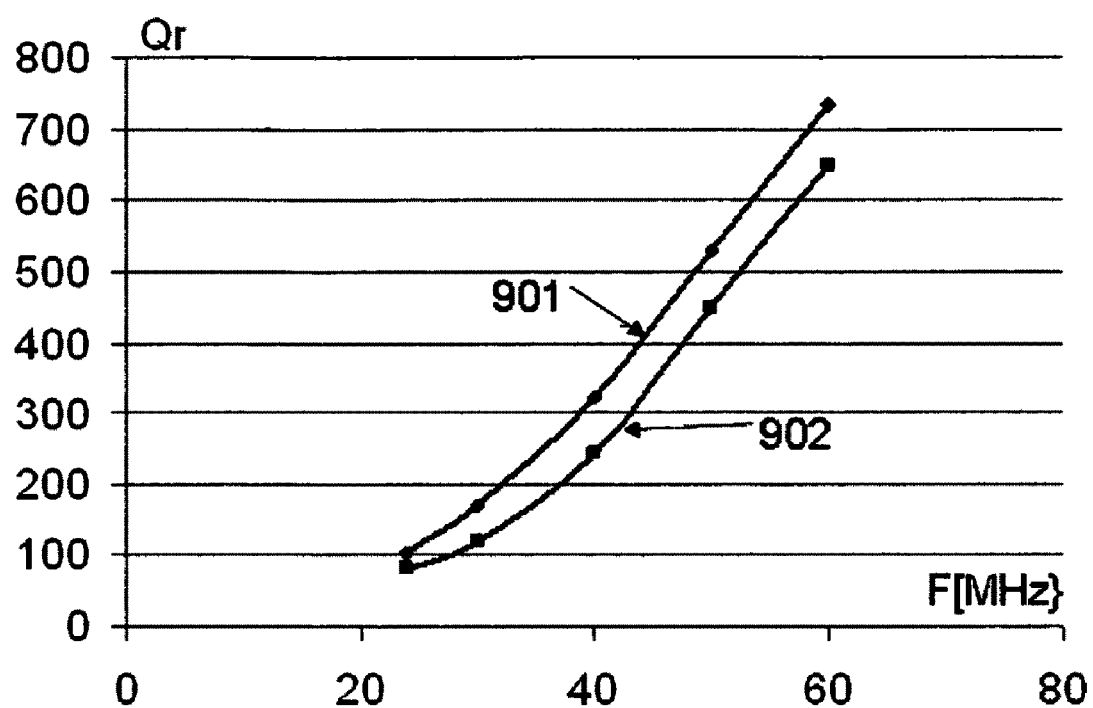
FIG. 9 illustrates dependence of the relative change in the Q-factor as a function of frequency. As a test sample, the cement-based composition 795 was used. The samples were given the following designations: 901 (bad sample); 902 (good sample). Measurements were carried out on a capacitive primary transducer designated as EC-5C.
Figure 10:
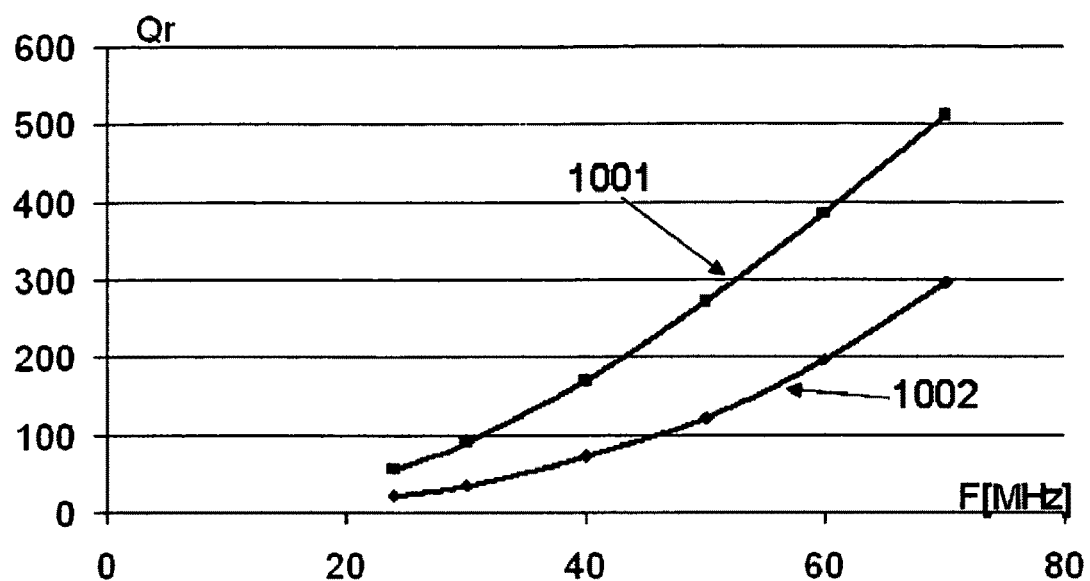
FIG. 10 illustrates dependence of relative change of material Q-factor as a function of frequency. As a test sample, the cement-based composition 795 was used. The samples were given the following designations 1001 (bad sample); 1002 (good sample). Measurements were carried out on a capacitive primary transducer EC-7C.

On the basis of the comparative analysis of data in FIGS. 9-11, one can conclude that a capacitive transducer with large electrode areas and a platform surface covered with copper foil such as EC-7C has a higher sensitivity and allows better determination of differences among samples of powdered materials with various properties. And this sensitivity is demonstrated at each frequency level.

Example 5

Figure 12:
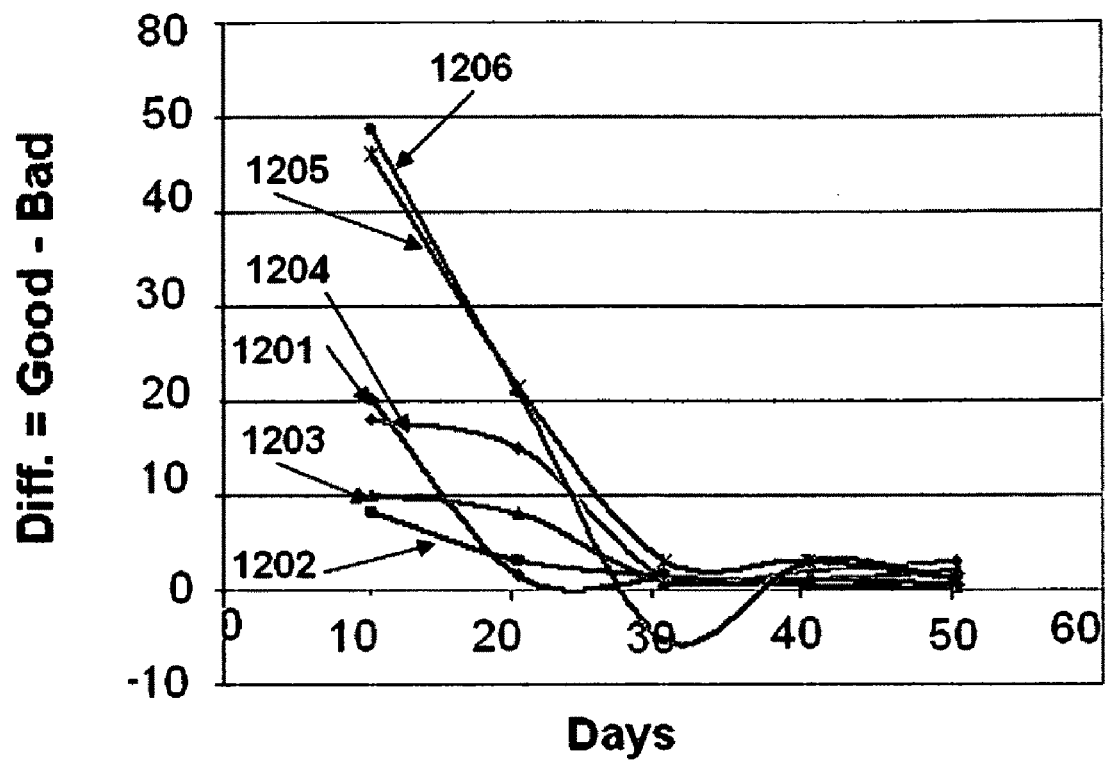
FIG. 12 shows results of testing "good" and "bad" samples of a cement-based composition after it has been stored for 50 days 1201, 1202, and 1203 are "bad" Samples, and 1204, 1205, and 1206 are "good" samples; The frequency of the measurement was 70 MHz.

The research that had been conducted earlier also gave the following result. Within a 50 days period of measuring parameters of "good" and "bad", the sample characteristics tended to become similar. This may be caused by aging of the "good" samples. Results of comparative evaluation of "Good" and "Bad" samples, which have been stored for a period of 50 days, are presented in FIG. 12 and Table 6. At the beginning of the measurements the difference in the value of a quantity measurement parameters for the fresh "Good" and "Bad" samples was approximately 50 relative units at a frequency of 70 MHz.

TABLE 6

Results of comparative evaluation of "Good" and "Bad" samples of cement composition, which have been stored for a period of 50 days.

| | Time, days | | | | |
|---|---|---|---|---|---|
| Quality | 10 | 20 | 30 | 40 | 50 |
| Bad | 20.2 | 1.5 | 1.1 | 1.0 | 0.5 |
| Bad | 8.2 | 3.0 | 1.4 | 0.5 | 0.0 |
| Bad | 10.0 | 8.0 | 0.9 | 1.0 | 2.0 |
| Good | 18.0 | 15.0 | 1.5 | 2.0 | 3.1 |
| Good | 46.2 | 21.5 | 3.1 | 3.0 | 1.0 |
| Good | 48.7 | 20.8 | −5.3 | 3.0 | 1.0 |

The data in these Examples show the usefulness of the method and equipment of the present invention. For instance, the recommended method and instruments allow monitoring the aging of cement-based composites and ensure more precise control of powdered material quality in the process of manufacturing and storage. This is particularly important for quality control of construction materials.

Below results of the non-destructive evaluation of composition 797 with different level of aging are presented. This testing was carried out done on composition 797 based on cement that had been aged as follows:
1. Fresh
2. Aged # 1 storage for a period of one month
3. Aged # 2 (exposed to severe conditions.

Figure 13:
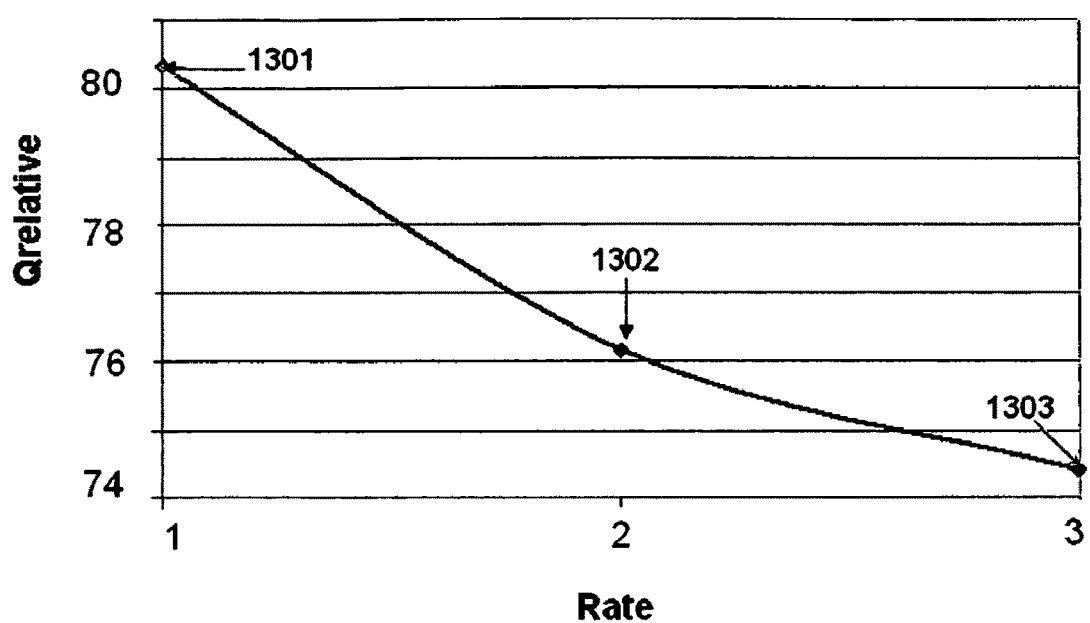
FIG. 13 shows results of evaluation of the cement composition 797 samples with different levels of the aging. Sample 1301 was fresh, samples 1302 was storage for one month, and sample 1303 was exposed to severe aging conditions.

Results of testing samples 797 are presented in Table 7 and FIG. 13.

TABLE 7

Numerical values of informative parameter Q.

| | 90 kHz | | |
|---|---|---|---|
| | Fresh | Aged 1 | Aged 2 |
| Qrelative | 81 | 70 | 70 |
| | 80 | 77 | 76 |
| | 78 | 74 | 71.5 |
| | 82 | 81 | 80 |
| | 80 | 75 | 72 |
| | 81 | 80 | 77 |
| Average: | 80.33 | 76.17 | 74.42 |

In FIG. 13, a smooth change of an informative signal $Q_{relative}$ as a function of the degree of aging of the test cement is shown. Results of evaluation presented in FIG. 12, Table 6 and FIG. 13, and Table 7 indicate that the method and device that comprise the present invention allow determination of the level of powdered sample aging.

Example 6

Figure 14:
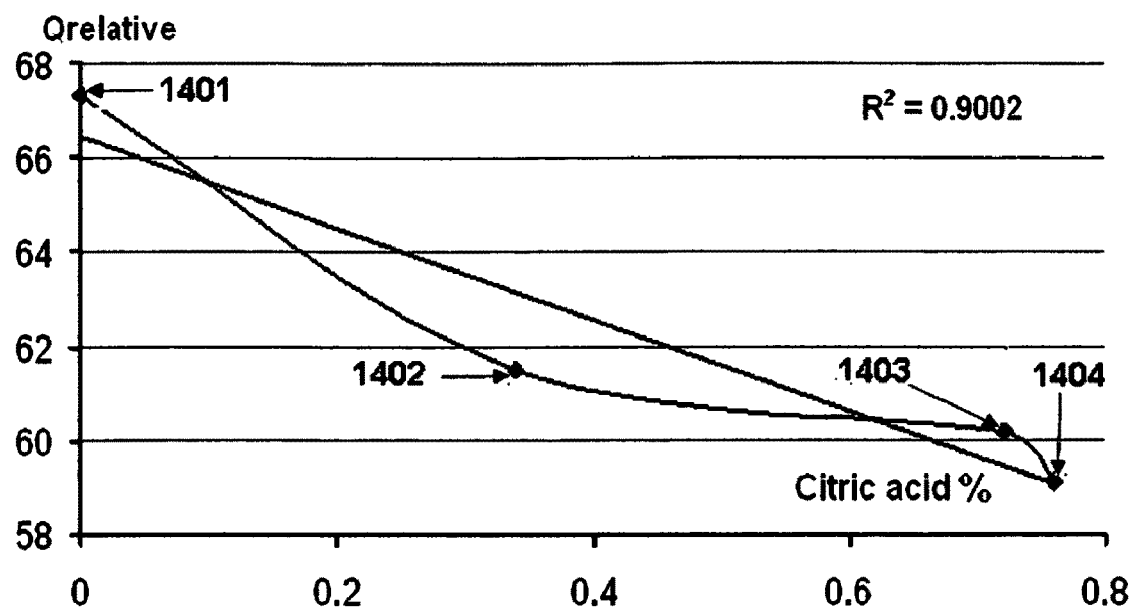
FIG. 14 shows results of testing of cement-based composition 941 samples with different level of acid content: 1401 was a "good" samples, 1402 had a 0.37% citric acid, 1403 had a 0.75% citric acid content, and 1403 was designated as a "bad" sample.

In this Example, results of the non-destructive evaluation of compositions with different citric acid content are described. This testing was done with samples based on the composition 941 with designations and citric acid content as follows:
1. 941 Good
2. 941 Bad
3. 941+0.75% citric acid
4. 941+0.37% citric acid In FIG. 14 the change of an informative signal as a function of the percent of the acid in the 941 cement-based composition is shown. From the analysis of the graph in FIG. 14, it is clear that the method allows unequivocal distinction between 941 "Good" samples and "Bad" samples.

Example 7

Powder residue on the electrodes after measurement causes some error when Qo is measured. To determine effect of powder level in between the electrodes on the error of Qo value, a separate investigation was conducted.

Measurements while filling the space between the electrodes to different quantity of the powder were carried out. Various powder quantities were used while the space between the electrodes was being filled. In Table 8, data on measuring Q-factor are shown for the cases when powder content, prior to measuring Qo value, was 70% and 30% of maximum content It was noticed that the error is higher when the residual increased. Results are presented in the Table 8.

TABLE 8

Effect of powder content in the space between electrodes on the error in the Q-factor.

|   | F MHz | Q | | | Measurement error (%) | |
|---|---|---|---|---|---|---|
| # | | Sensor without powder | Sensor with 70% of powder | Sensor with 30% of powder | Sensor with 70% of powder | Sensor with 30% of powder |
| 1 | 24 | 87 | 81.3 | 84.7 | 6.6 | 2.6 |
| 2 | 30 | 100 | 84 | 89.2 | 16.0 | 10.8 |
| 3 | 40 | 120 | 90 | 105 | 25.0 | 12.5 |
| 4 | 50 | 143 | 108 | 127.3 | 24.4 | 10.97 |
| 5 | 60 | 163 | 79.8 | 134.5 | 51.04 | 17.48 |

As the data in Table 8 show, residual powder can significantly affect the results of measurements.

Example 8

In the transducer design, an emitter of low frequency ultrasound (longitudinal oscillation) was used to provide vibration. Transmitting of ultrasound oscillation was switched on when the transducer was taken out of powder. In this way the electrode plates and the space between them were cleaned of powder residual after measurement of each parameter monitored.

At the same time it is appropriate to use longitudinal oscillation ultrasound when a transducer is immersed in the test powder. As our research showed, this would lead to condensing or uniform compacting of the test powder tested and ensure its even distribution in the space between electrodes.

CLOSURE

While various embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An electromagnetic device for rapid non-destructive quality control of physical and chemical properties of powdered materials by means of an electric field in the space between electrodes of a capacitive sensor, said system comprising;

measuring electro capacitive sensor having periodic structure with electrodes that can be flat parallel rectangular electrodes, or multiple flat parallel electrodes, or cylindrical electrodes including a combination of two concentric hollow cylinders or cylindrical segments;

ultrasonic energy component for removal of residual powder from the sensor, and for obtaining an uniform amount of powdered material between the electrodes of said capacitance sensor when immersing the transducer into powder material, said ultrasonic device being mounted together with a measuring electro capacitive transducer in a common case;

managing capacitive transducer with coplanar electrodes;

inductance coil, which together with a working capacitive transducer, constitutes a resonant circuit;

alternating current signal generator having selectable output frequencies;

circuit for measuring of self-capacitance and Q-factor of the resonance circuit containing said capacitive sensor;

power generator for an electromagnetic acoustic transducer to produce agitating vibration;

circuit for measuring the capacitance of a capacitive sensor;

circuit for measuring the agitating vibration produced by said electromagnetic acoustic transducer;

circuit for measuring the phase of the generator;

circuit for measuring frequency of the harmonic oscillations produced by the AC signal generator;

circuit for determining capacitance of a working transducer in powdered material;

circuit for ascertaining the digital value of the correcting signal;

circuit for ascertaining digital value of the informative signal;

circuit for the distinguishing between of high-quality and poor-quality powdered materials which have been tested based on average informative parameter values from multiple tests;

suitable data display monitor.

2. Device as in claim 1, wherein the measuring transducer include electrodes that are the sources of electric field wherein said electrodes are made as a continuation of the case exterior and are dielectric plates, mounted symmetrically, of the same dimensions; namely, having a thickness of 1-2 mm and wherein the lower interior plate part is covered with a copper coil of thickness 10-12 g, the distance between said plates being 5-8 mm, and the ratio of the total area of the dielectric transducer to the total area covered with copper foil is between 1.5:1 and 1.7:1.

3. Device as in claim 1, wherein the working capacitive sensor includes at potential and grounded electrodes, with grounded electrodes positioned on both sides of each potential electrode.

4. Device as in claim 1, wherein the copper electrode surface is coated with a good quality varnish that is high frequency in electrical terms having a thickness of 10 microns, said varnish coat being evenly dispersed over the electrode surface.

5. Device as in claim 1, wherein the lower ends of the flat and/or cylindrical dielectric electrodes have flats that are 4 mm in length with an angle of 70° to the interior wall.

6. Device as in claim 1, wherein the electrodes of managing coplanar transducer are mounted on outer surface of dielectric case, on two sides opposite the upper edge of the working transducer electrodes.

7. Device as in claim 1, wherein in the transducer case there is a sweep generator that can be set for specific working frequencies, and wherein is a circuit for encoding the measured parameters and sending them to the main electronic unit.

8. Device as in claim 1, wherein the electrodes of the capacitive transducer have openings in the upper part, through which powder density evenness is attained, when the space between electrodes is filled with powder in the process of immersing the transducer or sensor in the powdered material being tested.

* * * * *